United States Patent [19]

Ogura et al.

[11] Patent Number: 5,707,643
[45] Date of Patent: Jan. 13, 1998

[54] BIODEGRADABLE SCLERAL PLUG

[75] Inventors: Yuichiro Ogura, Kyoto; Yoshito Ikada, Uji, both of Japan

[73] Assignee: Santen Pharmaceutical Co., Ltd., Osaka, Japan

[21] Appl. No.: 665,047

[22] Filed: Jun. 7, 1996

Related U.S. Application Data

[63] Continuation of Ser. No. 325,194, filed as PCT/JP94/00273 Feb. 23, 1994 published as WO94/18921 Sep. 1, 1994, abandoned.

[30] Foreign Application Priority Data

Feb. 26, 1993 [JP] Japan ................................ 5-062814
Mar. 4, 1993 [JP] Japan ................................ 5-069457

[51] Int. Cl.$^6$ ...................................................... A61F 2/14
[52] U.S. Cl. ......................... 424/428; 424/426; 424/427
[58] Field of Search ............................. 424/426, 427, 424/428; 514/772.3

[56] References Cited

U.S. PATENT DOCUMENTS

| | | | |
|---|---|---|---|
| 4,439,198 | 3/1984 | Brightman, II et al. | 604/890.1 |
| 4,863,457 | 9/1989 | Lee | 604/891.1 |
| 5,098,443 | 3/1992 | Parel et al. | 424/428 |
| 5,194,473 | 3/1993 | Shinoda et al. | 524/263 |

FOREIGN PATENT DOCUMENTS

| | | |
|---|---|---|
| 0 488 401 | 6/1992 | European Pat. Off. |
| 4-364857 | 12/1992 | Japan . |
| 5-17370 | 1/1993 | Japan . |
| 2 156 684 | 10/1985 | United Kingdom . |

OTHER PUBLICATIONS

Isbey et al., "New Scleral Plugs for Use During Vitrectomy", pp. 797–799, Am. Journal of Ophthalmology, 91, No. 6, Jun. 30, 1981.

Isbey et al, "New Sclereal Plugs for use during Vitrectomy", pp. 797–799, Am. Journal of Opthalmology. 91, No. 6, Jun. 30, 1981.

*Primary Examiner*—Carlos Azpuru
*Attorney, Agent, or Firm*—Frishauf, Holtz, Goodman, Langer & Chick, P.C.

[57] ABSTRACT

The present invention relates to a scleral plug made of lactic acid copolymer; a scleral plug containing a drug that is designed to gradually release the drug into a vitreous body; and a scleral plug that is used to treat or prevent diseases of the retina or to promote recovery from damage after vitreous surgery taking advantage of its sustained release action for drug delivery.

17 Claims, 1 Drawing Sheet

BIODEGRADABLE SCLERAL PLUG

This application is a Continuation of application Ser. No. 08/325,194, filed Oct. 14, 1994, abn, which is the U.S. national phase application of International Application No. PCT/JP94/00273 filed Feb. 23, 1994, published as WO94/18921 Sep. 1, 1994.

TECHNICAL FIELD

The present invention relates to a biodegradable scleral plug and a technique to attain sustained release of a drug into a vitreous body with the use of the scleral plug including the drug. Moreover, the present invention relates to a scleral plug that can be used to treat or prevent diseases of the retina or to promote recovery from damage after vitreous surgery while taking advantage of the sustained release of a drug.

BACKGROUND OF THE INVENTION

A vitreous body is one of intraocular tissues that is viscous, transparent, and gel-like. A vitreous body consists mainly of water and includes components comprising collagen fibers and hyaluronic acid. The retina is the most inner tissue layer of the eye. It covers a vitreous body and is in direct contact therewith. Diseases of the retina are generally intractable and some of the diseases are accompanied by opacity of the vitreous body. Examples of such diseases are retinal hemorrhage caused by various damage, proliferative vitreoretinopathy accompanied by vascularization and proliferation of retinal cells, retinal detachment and retinoblastoma.

Eye diseases are generally treated by instillation of drugs. However, drugs can barely reach the retina or vitreous body by instillation. Moreover, the blood-aqueous barrier reduces delivery of effective concentration of a drug to the retina or a vitreous body even by a systemic administration, e.g., intravenous administration. It is not practical to inject a drug directly into a vitreous body, because injection of a high concentration of a drug may cause disorders of intraocular tissues and the procedure for repeated injection is laborious and may cause infection.

Some diseases are treated by intraocular surgery. For example, in the case of vitreous hemorrhage, the opaque vitreous body is excised, and in the case of proliferative vitreoretinopathy, the proliferative tissues and the vitreous body are excised. In the case of retinal detachment, the vitreous body is excised and an artificial vitreous body such as silicone is used to hold the retina steady. In vitreous surgery, the sclera that is the eyeball wall is incised at three sites; a site to irrigate physiological irrigating solution into the eye, a site to insert a guide that is used to light up the intraocular portion, and a site to insert tools for excision of a vitreous body, such as a cutter. A scleral plug made of metal may be used temporarily to insert tools into the eye or remove them (Am. J. Ophthalmol. 91, 797 (1981)), but the incisions are finally sutured to complete surgery.

For medicinal treatment of diseases of the retina or diseases of the vitreous body, a direct injection of drugs into the vitreous body is used. Methods for treating diseases have been studied in which microspheres or liposomes were used to release drugs slowly (Invt. Ophthalmol. Vis. Sci. 32, 1785 (1991)).

Recently, polymers from lactic acid have been studied as biodegradable polymers. Application studies of such polymers are reported, for example, as a substance to fix fractures of bones (Japanese Unexamined Patent Publication 29663/91), as a suture for surgery (Japanese Unexamined Patent Publication 501109/92), or as a vehicle for an intraocular implantation (Japanese Unexamined Patent Publication 22516/88). Sustained release of drugs with the use of poly(lactic acid) has also been studied (J. Med. Chem. 16, 897 (1973)). Furthermore, sustained release preparations for intraocular implantation using low molecular-weight poly (lactic acid) have been reported (Japanese Unexamined Patent Publication 17370/93).

While methods for gradually releasing drugs into a vitreous body using microspheres or liposomes are known, a need still exists for an innovation to readily control the release of drugs over a long period of time. To attain that object, we focused attention on the above-mentioned metallic scleral plug, which has been used as a temporary plug for incisions during vitreous surgery.

The objects to be attained by the present invention are basically as follows.

A first object of the present invention is to provide a scleral plug which can firmly plug an incision after vitreous surgery and need not removed.

Another object of the present invention is to provide a method of releasing drugs gradually into the intraocular tissues, where drugs are very difficultly delivered, for a long period of time to make it possible to administer drugs safely and effectively.

A further object of the present invention is to provide a convenient method of administering drugs that can be used clinically taking advantage of a scleral incision, after vitreous surgery.

DISCLOSURE OF THE INVENTION

As the result of our research on material for a scleral plug that need not be removed after surgery, we found that by using a lactic acid copolymer as the plug material, a scleral plug that is gradually degraded in the eye tissues and absorbed into the tissues, is safe to the highly sensitive tissues of the eye, can be prepared. Meanwhile, various properties are further desired to be provided to a scleral plug. Desired properties include maintaining the function to plug a scleral incisions for a required period, being degraded and absorbed in the required period, being easily handled during surgery, and so on. First, we examined a range of molecular weights for the lactic acid copolymer and the molar ratio of lactic acid units in the lactic acid copolymer which should satisfy the desired conditions, and found that it is preferable that the weight-average molecular weight of the lactic acid copolymer is in the range from 10,000 to 1,000,000 and the molar ratio of lactic acid units in the lactic acid copolymer is in the range from 50 to 100 mole %. Further, as a result of our study on the shape of a scleral plug, we found that it is preferable for a scleral plug to have a nail-like shape comprising a head portion, which prevents the plug from dropping into the inner site of eye, and a shaft portion, which is inserted through a scleral incision into the vitreous body. In particular, it is preferable that the end of the shaft portion is pointed, i.e., it is an acute-angled shape, such as pyramidal or conical, to prevent complication damage which may be caused when the plug is inserted.

We also studied a method to release a drug gradually into a vitreous body, and found that the object to release a drug gradually can be attained by allowing the drug to be contained in a scleral plug made of lactic acid copolymer, inserting the plug through a scleral incision into the vitreous body, and putting the end portion of the plug into the vitreous body. The insertion of the plug is usually carried out at a site of pars plana. It is possible to design the scleral plug of the present invention to enable a drug to be released depending on a desired releasing period by altering the molecular weight and/or the molar ratio of lactic acid units of the lactic acid copolymer. Because the plug is made of a biodegradable polymer, we found that the scleral plug of the present invention need not be removed after the drug is completely released, which could make it possible to attain effectively the object of the present invention. We also found that the scleral plug of the present invention could be inserted not only through an incision from vitreous surgery but also through a small opening directly made into a vitreous body through the sclera because the scleral plug of this invention can easily be inserted into the vitreous body through the sclera. Therefore, the scleral plug of the present invention can be used to treat or prevent diseases of the retina even if vitreous surgery is not carried out. If a very long drug-releasing period is needed, additional scleral plugs of the present invention can be inserted. If a high concentration of the drug is needed, a plurality of the plugs of the present invention can be inserted simultaneously.

The present invention relates to a scleral plug made of lactic acid copolymer; a scleral plug containing a drug that is designed to gradually release the drug into a vitreous body; and a scleral plug that is used to treat or prevent diseases of the retina or to promote recovery from damage after vitreous surgery taking advantage of its sustained release effect for drug delivery. As used herein, "a lactic acid copolymer" generally means a copolymer comprising lactic acid units and glycolic acid units. However, malic acid, glyceric acid, or tartaric acid, etc. can also be used instead of glycolic acid. "A lactic acid copolymer" also includes a copolymer consisting of lactic acid units in a molar ratio of 100%, i.e., poly (lactic acid). A lactic acid unit may be in a L-, D-, or DL-form.

A scleral plug needs to be strong enough not to break or chip by manipulation with a pincette during surgery. Moreover, a scleral plug needs to have properties to release a drug slowly during the desired period of time for treatment, etc., and to be degraded in eye tissues and absorbed into the tissues afterwards. The properties of a scleral plug can be determined by the weight-average molecular weight of the copolymer, the ratio of lactic acid units and glycolic acid units (unless otherwise stated the ratio is represented on a molar basis), and the like. To simplify the following explanation hereinafter, a copolymer consisting of lactic acid units and glycolic acid units is taken as a sample of copolymers. The degree of degradation of the copolymer essentially depends upon the degree of crystallinity and water absorptivity of the copolymer. As either the ratio of lactic acid units or that of glycolic acid units becomes higher, the degree of crystallinity becomes higher and the degradation rate becomes lower. When the ratio of lactic acid units and glycolic acid units is 50/50, the degradation rate is the highest. As the ratio of glycolic acid units in the copolymer becomes higher, the characteristics of polyglycolic acid appear and result in an increase of hydrophilicity, because polyglycolic acid is slightly more hydrophilic than poly(lactic acid). Therefore, the water absorptivity becomes higher and the degradation rate becomes higher. If the ratio of glycolic acid units is over 50%, the plug is difficult to prepare, because the copolymer is not easily dissolved in the usual organic solvents that are used to prepare the plug. Therefore, in consideration of the above mentioned characteristics of glycolic acid units, the ratio of glycolic acid units is preferably 50% or less.

The degradation rate of the plug is generally in proportion to the weight-average molecular weight of the copolymer.

Therefore, as the molecular weight becomes higher, the degradation rate becomes lower.

When the plug is prepared, the ratio of lactic acid units and glycolic acid units and the molecular weight of the copolymer can be selected by taking account of the above-mentioned characteristics of the composition and functions required of the plug. The molar content of the lactic acid units in the copolymer for the scleral plug of the present invention is preferably 50 to 100%. The molar content of the glycolic acid units is preferably 0 to 50%. The molecular weight of the copolymer affects the strength of the plug. As the molecular weight becomes higher, the strength of the plug is increased. Taking into consideration the strength required for the plug, the molecular weight of the copolymer is preferably 10,000 or more. When the molecular weight is too high, the degradation rate of the plug becomes low and the molding of the plug becomes difficult. Accordingly the molecular weight of the copolymer is preferably 1,000,000 or less. Thus, the weight-average molecular weight of the copolymer is preferably from 10,000 to 1,000,000 and can be selected from the range depending on the application purposes.

The weight-average molecular weight of the copolymer and ratio of lactic acid units and glycolic acid units are determined depending upon the period of time to maintain the effective concentration of the drug. The period of time to maintain the effective concentration of the drug, i.e., a required releasing period, is mainly determined depending upon the disease to be treated, the symptoms, and the effects of the drug. The scleral plug of the present invention can be preferably used to treat various kinds of retina diseases or to promote recovery from damage after vitreous surgery. For example, proliferative vitreoretinopathy, viral infection, postoperative inflammation, postoperative infection can be treated or prevented. The releasing period of a drug can be controlled in the range from one week to six months by selecting the molecular weight of the copolymer or the ratio of lactic acid units and glycolic acid units.

If the desired releasing period is relatively short, such as one to two weeks, the molecular weight of the copolymer can be about 10,000 to 100,000 and preferably about 10,000 to 50,000, and more preferably 20,000 to 40,000. If the desired releasing period is about two weeks to one month, the molecular weight of the copolymer can be about 10,000 to 200,000 and preferably about 20,000 to 100,000, and more preferably 20,000 to 50,000. If the desired releasing period is long, i.e., more than one month, for example, one to six months, the molecular weight of the copolymer can be about 10,000 to 1,000,000 and preferably about 20,000 to 400,000, and more preferably 40,000 to 200,000. As described above, the releasing period of a drug can also be controlled by altering the molar ratio of lactic acid units and glycolic acid units. Taking into consideration the releasing period of the drug and the degree of degradation of the plug, an appropriate molecular weight and the ratio of lactic acid units and glycolic acid units in the copolymer are selected. The ratio of lactic acid units and glycolic acid units is in the range from 100/0 to 50/50.

In more detail, when the drug is doxorubicin hydrochloride, which is useful for proliferative vitreoretinopathy, the releasing period for the drug is preferably two weeks to one month. The molecular weight of the copolymer of the scleral plug is about 10,000 to 200,000, preferably about 20,000 to 100,000, more preferably about 20,000 to 50,000 and the ratio of lactic acid units and glycolic acid units is 100/0 to 50/50, preferably 80/20 to 50/50, more preferably about 80/20 to 70/30. When the drug is ganciclovir, which is useful for viral infection, the releasing period of the drug is more than one month, for example one to six months, preferably about four to six months. The molecular weight of the copolymer of the scleral plug is about 10,000 to 1,000,000, preferably about 20,000 to 400,000, more preferably about 40,000 to 200,000 and the molar ratio of lactic acid units and glycolic acid units is 100/0 to 50/50, preferably 80/20 to 50/50, more preferably about 80/20 to 70/30.

A plurality of the scleral plugs of the present invention can be used simultaneously and successively or additionally. Therefore, if a high concentration of the drug is needed for clinical treatment, a plurality of the plugs can be used simultaneously, and if a releasing period of the drug should be extended, the plugs can be used successively or additionally. Thus, even if a desired amount of the drug can be hardly contained in a piece of plug, a desired amount of the drug can be released into the vitreous body by using plugs simultaneously or successively.

Japanese Unexamined Patent Publication 17370/93 discloses the use of poly(lactic acid) in a sustained release preparation that can be implanted in eyes, but the poly(lactic acid) is low in average molecular weight (up to about 7000). Such low molecular-weight poly(lactic acid) can not be used as a material for the scleral plug, because the above-discussed desired properties cannot be obtained.

A preferred shape of the scleral plug is a nail-like shape comprising a head portion, which prevents the plug from dropping into the eye ball, and a shaft portion, which is inserted into a scleral incision. In particular, it is preferable that the end of the shaft portion be pointed, i.e., it is an acute-angled shape, such as, pyramidal or conical to prevent disease complication, which may be caused when the plug is inserted. Preferably, the head portion is formed in a hemispheric, disk-like or polygonal (e.g., hexagonal) shape and the shaft portion is formed in prismatic, columnar, or the like, shape. The following information on the sizes of the plug is given by way of explanation to make understanding the shape of the plug of the present invention easier. The length of the plug is normally about 6 mm, the diameter of the head portion is about 2 mm, the diameter or width of the shaft portion is about 1 mm, and the weight of the plug is about 9 mg. Of course, these sizes can be altered depending upon the amount of the drug to be contained. A release of the drug into the vitreous body can be attained by diffusion of the drug accompanying hydrolysis of the copolymer of the plug. The plug is not required to be removed because it is degraded in eye tissues and absorbed into the tissues. The amount of the released drug can be adjusted to a level that can maintain the effective concentration in the vitreous body and does not cause retinal damage, since the retina is easily damaged by contact with a high concentration of drugs. The amount of the released drug can be controlled by selecting the content of the drug in the plug, the molecular weight of the copolymer and a ratio of lactic acid units and glycolic acid units. The amount of the drug to be contained in the plug can be selected depending on the period over which the effective concentration of the drug should be maintained. The period can be selected depending on the disease to be treated or prevented, the symptoms, the properties or effects of the drug, etc. The period to maintain the effective concentration of a drug is normally in the range of a week to six months. For example, when antitumor agents, such as doxorubicin hydrochloride, which can be used to treat proliferative vitreoretinopathy, are used, a standard releasing period of the drug is in the range from about two weeks to one month. When antiviral agents such as ganciclovir, which can be used to treat viral infections, are used, a standard releasing period of the drug is more than one month, e.g., about one month to six months. When antiinflammatory agents, such as steroids, which can be used to treat postoperative inflammation, are used, a standard releasing period of the drug is in the range from about two weeks to one month. When antibiotics, which can be used to treat postoperative infections, are used, a standard releasing period of the drug is in the range from about one week to two weeks. When antifungal agents, which can be used to treat mycotic infections, are used, a standard releasing period of the drug is more than one month, for example, in the range from about one month to two months. A variety of drugs that are useful to treat or prevent various diseases of the retina or to promote recovery from damage after vitreous surgery, can be used. The characteristic of the present invention is a technology to apply biodegradable lactic acid copolymers and the drug itself does not limit applications of the present invention. Various kinds of drugs such as antitumor agents, antibiotics, antiinflammatory agents, antiviral agents or antifungal agents can be used.

General methods of preparing the plug of the present invention comprises the steps of synthesizing a lactic acid copolymer according to a known method, dissolving the copolymer in an organic solvent, such as methylene chloride, acetonitrile, acetic acid, or the like, adding a drug to the mixture, removing the solvent, and forming a plug from the obtained powder. The lactic acid copolymer can be prepared by e.g., polymerizing lactic acid or the cyclic dimer thereof and a comonomer such as glycolic acid or the cyclic dimer thereof in the presence of a catalyst such as tin octylate and lauryl alcohol. A bulk polymerization is preferable, but the polymerization methods are not limited.

BEST MODE OF CARRYING OUT THE INVENTION

Processes for producing scleral plugs for sustained release of drugs, i.e., doxorubicin hydrochloride, which can be used to treat or prevent proliferative vitreoretinopathy, and ganciclovir, which can be used to treat or prevent viral infection, are exemplified below. The following examples are given to make the present invention clearly understood and shall not limit the scope of the present invention.

(Productional Example 1)

Figure 1:
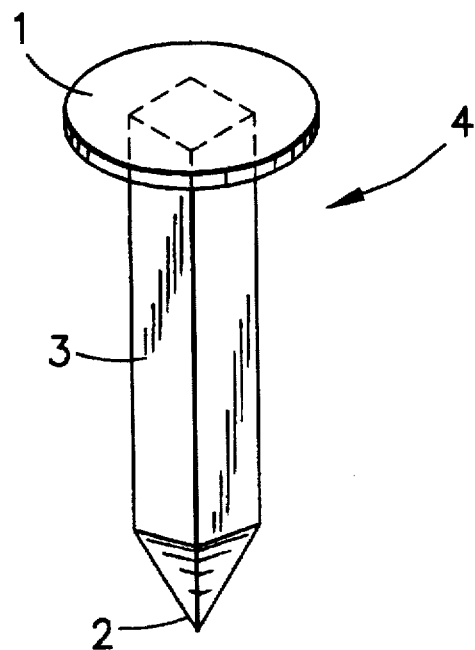
FIG. 1 is a perspective view of the scleral plug prepared in the Productional example 1 below.

First, an L-lactic acid/glycolic acid (in a molar ratio of 75/25) copolymer was synthesized in the presence of a catalyst consisting of tin octylate and lauryl alcohol by a bulk ring-opening polymerization. The weight-average molecular weight of the obtained copolymer was 38,000. After the copolymer (198 mg) was dissolved in 2 ml methylene chloride, doxorubicinhydrochloride (2 mg) was dispersed in the solution while stirring. The resulting dispersion was cast on a Teflon sheet to obtain an L-lactic acid/glycolic acid copolymer sheet containing doxorubicin hydrochloride. Then the scleral plug shown in FIG. 1 was formed from the sheet by a cutting and skiving process.

The scleral plug 4 is a nail-like shape consisting of a disk-like shaped head portion 1 and a shaft portion 3 of a square pillar. The end 2 of the shaft portion 3 is pyramidal.

(Productional Example 2)

Figure 2:
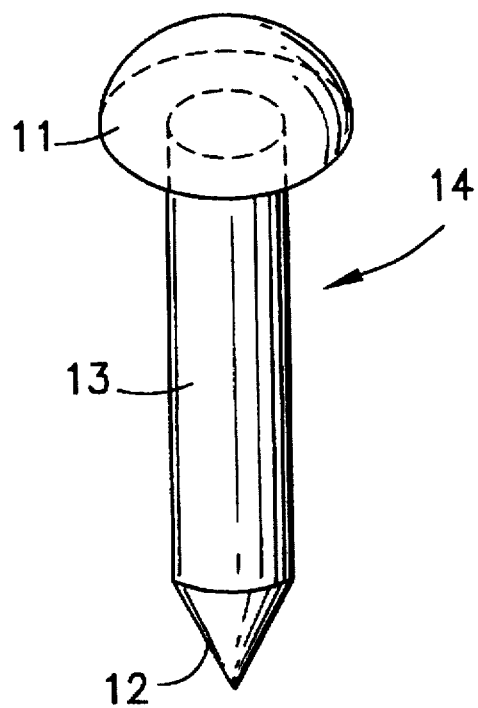
FIG. 2 is a perspective view of the scleral plug prepared in the Productional example 2 below.

1000 mg of a copolymer (molar ratio of L-lactic acid unit/glycolic acid unit: 75/25, the weight-average molecular weight was 40,000) prepared as described in Productional example 1 and doxorubicinhydrochloride (5 mg) were dissolved in 5 ml of acetonitrile/water (9/1). The solvent was then removed from the solution by lyophilization. The resulting powder was formed into a scleral plug under heating to obtain the scleral plug shown in FIG. 2.

The scleral plug 14 is a nail-like shape consisting of a hemispheric head portion 11 and a columnar shaft portion 13. The end 12 of the shaft portion 13 is conical.

By similar methods to those as described above, a scleral plug which consists of L-lactic acid/glycolic acid in a molar ratio of 50/50, 70/30, or 80/20 and having a weight-average molecular weight of 10,000, 20,000, 50,000, 70,000, 100,000, or 200,000; and which contains doxorubicin hydrochloride by 0.1%, 0.3%, 0.5%, 1%, or 2% can be obtained. By using D-lactic acid or DL-lactic acid instead of L-lactic acid, a similar scleral plug can be obtained.

(Productional Example 3)

900 mg of a copolymer (DL-lactic acid/glycolic acid: 75/25, the weight-average molecular weight was 122,000) prepared as described in Productional example 1 and ganciclovir (100 mg) were dissolved in 15 ml of acetic acid and the mixture was lyophilized. The resulting powder was formed into a scleral plug under heating.

By similar methods to those described above, a scleral plug which consists of DL-lactic acid/glycollic acid in a molar ratio of 50/50, 70/30, or 80/20 and having a weight-average molecular weight of 10,000, 20,000, 40,000, 200,000, 400,000, or 1,000,000; and which contains ganciclovir by 1%, 2%, 5%, 10%, 15%, or 20% can be obtained. By using L-lactic acid or D-lactic acid instead of DL-lactic acid, a similar scleral plug can be obtained.

(Productional Example 4)

900 mg of poly(L-lactic acid) (the weight-average molecular weight was 95,000) and ganciclovir (100 mg) were dissolved in 15 ml of acetic acid and then the mixture was lyophilized. The resulting powder was formed into a scleral plug under heating.

By similar methods to those described above, a scleral plug having a weight-average molecular weight of 10,000, 20,000, 40,000, or 200,000; and which contains ganciclovir by 1%, 2%, 5%, 10%, 15% or 20% can be obtained. By using poly (DL-lactic acid) or poly(D-lactic acid) instead of poly (L-lactic acid), a similar scleral plug can be obtained.

Sustained release effect of the drug, safety and degradation rate of the scleral plug which contains doxorubicin hydrochloride as an example of a drug were tested. The scleral plug containing doxorubicin hydrochloride prepared in Productional example 1 above was used.

(1) In vitro tests

The scleral plug was incubated in an isotonic phosphate buffer, (pH 7.4) at 37° C. 1, 3, 7, 14, 21, and 28 days after starting of the incubation, the amount of eluted doxorubicin hydrochloride was measured with a fluorescent spectrophotometer. The results are shown in Table 1, where the eluted amounts are represented by wt % to the amount of doxorubicin hydrochloride that is originally contained in the scleral plug (100%). The results were shown by the mean value of three test samples.

TABLE 1

| Day | The amount of eluted drug (%) |
| --- | --- |
| 1 | 6.2 |
| 3 | 9.5 |
| 7 | 13.4 |
| 14 | 17.2 |
| 21 | 22.2 |
| 28 | 26.0 |

As shown in Table 1, doxorubicinhydrochloride was eluted slowly for four weeks. The results prove the sustained release effect of the drug, which is the object of the present invention. During the test period, disintegration of the plug was not observed.

(2) In vivo tests

Vitreous surgery was performed on one eye of each of ten pigmented rabbit. After two weeks, the scleral plug was inserted through the scleral incision and covered with conjunctiva. 1, 3, 5, 14, and 28 days after insertion, 0.2 ml aqueous humor was taken from vitreous cavity and stored at −80° C. The concentration of doxorubicin hydrochloride in the aqueous humor was measured by a high performance liquid chromatographic method. The results are shown in Table 2.

TABLE 2

| Day | The concentration of drug (ng/ml), mean value of ten eyes |
| --- | --- |
| 1 | 12.4 |
| 3 | 12.8 |
| 5 | 9.4 |
| 14 | 2.8 |
| 28 | 7.5 |

As shown in Table 2, doxorubicin hydrochloride was released gradually into the vitreous body for four weeks and the effective concentration was maintained (2 to 10 ng/ml) on each measuring day. Moreover, the concentration of the drug did not greatly rise at a time and accumulation of the drug in the vitreous body was not observed. The sustained release effect and the safety of the plug of the present invention were proved by this test.

(3) Toxicity tests (Histopathologic change in tissues)

The scleral plug was inserted through a scleral incision into the vitreous body of a pigmented rabbit and covered with conjunctiva. After one or three months, an eyeball was excised to observe histopathologic change in eye tissues with a light microscope. No histopathologic change was observed and the safety of the plug was proved. After the excision of an eyeball, the condition of the plug was also checked to ascertain degradation of the scleral plug. The result proves that the scleral plug of the present invention is slowly degraded in a living body.

(Change in retinal functions)

Vitreous surgery was performed on one eye of each of two pigmented rabbits and then the scleral plug was inserted through the scleral incision and covered with conjunctiva. One month after insertion, an electroretinogram was recorded and compared with the electroretinogram recorded before vitreous surgery and also compared with the electroretinogram of the other eye, which was not treated by vitreous surgery. No change in b wave was observed in every case. The result proved that the scleral plug of the present invention did not affect the functions of retina.

INDUSTRIAL APPLICABILITY

The present invention provides a scleral plug that effectively plugs an incision after vitreous surgery and is not required to be removed. The scleral plug enables a drug to be administered safely and effectively in intraocular tissues, where drugs hardly distribute, by releasing a drug gradually for a long period. Moreover, it is possible to find another conventional methods for administering a drug, e.g., a method involving the use of a scleral incision which is formed during vitreous surgery.

We claim:

1. A scleral plug made of a lactic acid copolymer of lactic acid units and glycolic acid units, and containing a drug characterized in that when the plug is inserted into a vitreous body of an eye, the drug is released slowly into the vitreous body; and wherein a scleral plug made of lactic acid copolymer comprising lactic acid units and glycolic acid units, the weight-average molecular weight of the copolymer is in the range from 10,000 to 1,000,000; the molar ratio of lactic acid units and glycolic acid units is in the range from 50/50 to 100/0; and said scleral plug has a nail-like shape comprising a head portion and a shaft portion, the end of the shaft portion being pointed.

2. The scleral plug according to claim 1, said plug is designed to release an effective concentration of said drug for about one to two weeks.

3. The scleral plug according to claim 1, wherein the weight-average molecular weight of the copolymer is in the range from 20,000 to 40,000, and said plug is designed to release an effective concentration of said drug for about one to two weeks.

4. The scleral plug according to claim 1, wherein the weight-average molecular weight of the copolymer is in the range from 10,000 to 200,000, and said plug is designed to release an effective concentration of said drug for about two weeks to one month.

5. The scleral plug according to claim 1, wherein the weight-average molecular weight of the copolymer is in the range from 20,000 to 50,000, and said plug is designed to release an effective concentration of said drug for about two weeks to one month.

6. The scleral plug according to claim 1, wherein said plug is designed to release an effective concentration of said drug for one month or more.

7. The scleral plug according to claim 1, wherein the weight-average molecular weight of the copolymer is in the range from 40,000 to 200,000, and said plug is designed to release an effective concentration of said drug for one month or more.

8. The scleral plug according to any one of claims 1 to 7, wherein the molar ratio of lactic acid units and glycolic acid units is in the range from 50/50 to 80/20.

9. The scleral plug according to any one of claims 1 to 7, wherein the molar ratio of lactic acid units and glycolic acid units is in the range from 70/30 to 80/20.

10. The scleral plug of claim 1 containing a drug for use in treating or preventing diseases of retina, wherein said drug is released gradually into a vitreous body and said scleral plug has a nail-like shape comprising a head portion and a shaft portion, the end of the shaft portion being pointed.

11. The scleral plug of claim 1 containing a drug for use in promoting a recovery from damage after vitreous surgery, wherein said drug is released slowly into a vitreous body and said scleral plug has a nail-like shape comprising a head portion and a shaft portion, the end of the shaft portion being pointed.

12. The scleral plug according to claim 4 or 5, wherein said drug is an antitumor agent.

13. The scleral plug according to claim 6 or 7, wherein said drug is an antiviral agent.

14. The scleral plug according to claim 4 or 5, wherein said drug is an antiinflammatory agent.

15. The scleral plug according to claim 2 or 3, wherein said drug is an antibiotics.

16. The scleral plug according to claim 6 or 7, wherein said drug is an antifungal agent.

17. A method for the treatment or prevention of diseases of the retina which comprises administering an effective amount of an effective drug into a vitreous body of the eye and wherein the drug is contained in a biodegradable scleral plug having a shaft portion and a head portion which releases the drug when inserted into the vitreous body, the administering of the effective amount of the drug comprising inserting the shaft portion only, of the biodegradable scleral plug into the vitreous body through the sclera, the head portion remaining outside the vitreous body; whereby the shaft portion is absorbed into the vitreous body and the drug is released gradually into the vitreous body from the scleral plug as the shaft is absorbed into the vitreous body.

* * * * *